United States Patent
Uehara Matsuoka et al.

(10) Patent No.: US 11,969,490 B2
(45) Date of Patent: *Apr. 30, 2024

(54) HAIR CONDITIONING COMPOSITION WITH ANTIMICROBIAL SYSTEM

(71) Applicant: The Procter & Gamble Company, Cincinnati, OH (US)

(72) Inventors: Nobuaki Uehara Matsuoka, Singapore (SG); Kai Wei Kelvin Lee, Singapore (SG)

(73) Assignee: The Procter & Gamble Company, Cincinnati, OH (US)

(*) Notice: Subject to any disclaimer, the term of this patent is extended or adjusted under 35 U.S.C. 154(b) by 101 days.

This patent is subject to a terminal disclaimer.

(21) Appl. No.: 17/350,088

(22) Filed: Jun. 17, 2021

(65) Prior Publication Data

US 2021/0401703 A1  Dec. 30, 2021

Related U.S. Application Data

(60) Provisional application No. 63/045,428, filed on Jun. 29, 2020.

(51) Int. Cl.
| | |
|---|---|
| A61K 8/04 | (2006.01) |
| A61K 8/02 | (2006.01) |
| A61K 8/06 | (2006.01) |
| A61K 8/34 | (2006.01) |
| A61K 8/35 | (2006.01) |
| A61K 8/36 | (2006.01) |
| A61K 8/37 | (2006.01) |
| A61K 8/44 | (2006.01) |
| A61K 8/49 | (2006.01) |
| A61Q 5/12 | (2006.01) |
| A61Q 17/00 | (2006.01) |

(52) U.S. Cl.
CPC ............ *A61K 8/042* (2013.01); *A61K 8/0233* (2013.01); *A61K 8/06* (2013.01); *A61K 8/068* (2013.01); *A61K 8/342* (2013.01); *A61K 8/345* (2013.01); *A61K 8/35* (2013.01); *A61K 8/361* (2013.01); *A61K 8/375* (2013.01); *A61K 8/44* (2013.01); *A61K 8/4946* (2013.01); *A61Q 5/12* (2013.01); *A61Q 17/005* (2013.01); *A61K 2800/21* (2013.01); *A61K 2800/30* (2013.01); *A61K 2800/33* (2013.01); *A61K 2800/34* (2013.01); *A61K 2800/412* (2013.01); *A61K 2800/805* (2013.01)

(58) Field of Classification Search
None
See application file for complete search history.

(56) References Cited

U.S. PATENT DOCUMENTS

| | | |
|---|---|---|
| 4,725,433 A | 2/1988 | Matravers |
| 5,968,492 A | 10/1999 | Noguchi et al. |
| 6,432,420 B2 | 8/2002 | Ellis et al. |
| 9,572,769 B2 | 2/2017 | Park et al. |
| 9,642,788 B2 | 5/2017 | Marsh et al. |
| 2001/0008630 A1 | 7/2001 | Pyles et al. |
| 2001/0008631 A1 | 7/2001 | Ellis et al. |
| 2006/0058205 A1 | 3/2006 | Ainger et al. |
| 2006/0078528 A1 | 4/2006 | Yang et al. |
| 2009/0071493 A1 | 3/2009 | Nguyen et al. |
| 2010/0105775 A1 | 4/2010 | Delong et al. |
| 2010/0330004 A1 | 12/2010 | Burgo |
| 2012/0070398 A1 | 3/2012 | Nagano et al. |
| 2014/0335036 A1 | 11/2014 | Marsh et al. |
| 2016/0015615 A1 | 1/2016 | Mann et al. |
| 2016/0175209 A1 | 6/2016 | Walker et al. |
| 2018/0098923 A1 | 4/2018 | Hutton, III |
| 2018/0110708 A1 | 4/2018 | Schrott |
| 2018/0333494 A1 | 11/2018 | Lane et al. |
| 2019/0282478 A1 | 9/2019 | Pesaro et al. |
| 2020/0056118 A1 | 2/2020 | Schulze et al. |
| 2020/0170931 A1 | 6/2020 | Lim et al. |
| 2020/0206127 A1 | 7/2020 | Lim et al. |

FOREIGN PATENT DOCUMENTS

| | | | |
|---|---|---|---|
| CA | 2330943 C | 12/2009 | |
| CN | 102178612 A | 9/2011 | |
| CN | 102988195 A | 3/2013 | |
| CN | 106551799 A | 4/2017 | |
| CN | 106619149 A | 5/2017 | |
| CN | 106726640 A | 5/2017 | |
| CN | 106726641 A | 5/2017 | |
| CN | 106726642 A | 5/2017 | |
| CN | 106726643 A | 5/2017 | |
| EP | 1344515 A1 | 9/2003 | |
| EP | 0964673 B1 | 10/2003 | |
| EP | 1752193 A1 * | 2/2007 | ............ A01N 31/04 |
| EP | 2774481 A1 | 9/2014 | |
| FR | 2730931 A1 | 8/1996 | |

(Continued)

OTHER PUBLICATIONS

Google English Translation of EP1752193A1 (Year: 2007).*
PCT Search Report and Written Opinion for PCT/US2021/037848 dated Nov. 11, 2021, 10 pages.
Anna Herman: "Antimicrobial Ingredients as Preservative Booster and Components of Self-Preserving Cosmetic Products", Current Microbiology, vol. 76, No. 6, Apr. 12, 2018, pp. 744-754, XP055619588, New York, ISSN: 0343-8651, DOI: 10.1007/s00284.
Anonymous: "What is Pentylene Glycol?", Jul. 27, 2019, XP055856110, Retrieved from the Internet:URL:https://nayaglow.com/blogs/news/what-is-pentylene-glycol[retrieved on Oct. 28, 2021], 10 pages.

(Continued)

*Primary Examiner* — Kyung S Chang

(74) *Attorney, Agent, or Firm* — John G. Powell; Kathleen Y. Carter

(57) ABSTRACT

A hair conditioner composition comprising: a) a fatty acid; b) a fatty alcohol; and c) an antimicrobial system comprising: i) glyceryl caprylate; and ii) one or more of 4-hydroxyacetophenone and pentylene glycol.

16 Claims, No Drawings

(56) References Cited

FOREIGN PATENT DOCUMENTS

| | | |
|---|---|---|
| JP | 2003238329 A | 8/2003 |
| JP | 5657191 B2 | 12/2014 |
| JP | 5969793 B2 | 7/2016 |
| WO | 0033807 A1 | 6/2000 |
| WO | 0051555 A1 | 9/2000 |
| WO | 0051556 A1 | 9/2000 |
| WO | 2007093271 A2 | 8/2007 |
| WO | 2020043269 A1 | 3/2020 |
| WO | 2020182318 A1 | 9/2020 |

OTHER PUBLICATIONS

Ayako Hirai et al: "Effects of 1-arginine on aggregates of fatty-acid/potassium soap in the aqueous media", Colloid and Polymer Science, Springer, Berlin, DE, vol. 284, No. 5, Feb. 1, 2006 (Feb. 1, 2006), pp. 520-528, XP019340539, ISSN: 1435-1536, DOI: 10.1007/S00396-005-1423-1.

All Office Actions; U.S. Appl. No. 17/350,069, filed Jun. 17, 2021.

All Office Actions; U.S. Appl. No. 17/350,079, filed Jun. 17, 2021.

Unpublished U.S. Appl. No. 17/350,069, filed Jun. 17, 2021, to first inventor Nobuaki Uehara Matsuoka et. al.

Unpublished U.S. Appl. No. 17/350,079, filed Jun. 17, 2021, to first inventor Nobuaki Uehara Matsuoka.

Database GNPD [Online] MINTEL, "Energizing Conditioner", dated Feb. 15, 2017, XP093041339, Database accession No. 4606289, 4 pages.

Database GNPD [Online] MINTEL, "Repairing Shampoo", date Jan. 11, 2016, XP093040981, Database accession No. 3719305, 3 pages.

Database GNPD [Online] MINTEL, "Shampoo", dated Jan. 7, 2019, XP093040972, Database accession No. 6239723, 3 pages.

Database GNPD [Online] MINTEL; "Conditioner", dated Sep. 17, 2011, XP093041340, Database accession No. 1619647, 3 pages.

BASF the Chemical Company, Eumulgin® CO 40 Innovadex® Product Datasheet, Aug. 19, 2014, 3 Pages.

BASF, Products, Eumulgin® CO 40, 2023, 2 Pages.

Bioderma, "Pigmentbio Foaming Cream", 2023, 2 Pages.

Fern, "An Afternoon with hair extraordinaire rossano ferretti, Creator of the method haircut", Nov. 1, 2017, 3 Pages.

Grazia, "News Flash: There's a New Bioderma Micellar Water on the Block", Apr. 14, 2020, 9 Pages.

Hebeloft, Dr. Groot Anti-Hair Loss Shampoo for Oily Scalp, 2023, 2 Pages.

Lim, "Insider Review: Dr Groot Might Just Salvage Your Hair Loss Problems", Beauty Insider Singapore, Oct. 9, 2021, 5 pages.

Rosasano Ferretti, Rejuvenating Shampoo, 6.8 oz, 2023, 2 Pages.

\* cited by examiner

HAIR CONDITIONING COMPOSITION WITH ANTIMICROBIAL SYSTEM

FIELD OF THE INVENTION

The present invention relates to a hair conditioning composition comprising a fatty acid, fatty alcohol, and an antimicrobial system.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. For example, some cationic surfactants, when used together with some high melting point fatty compounds and an aqueous carrier, are believed to provide a lamellar gel network matrix with a $L_\beta$ phase, which is suitable for providing a variety of conditioning benefits such as a slippery feel during the application to wet hair, softness, and a moisturized feel on dry hair.

But some consumers would prefer products that do not have cationic surfactant molecules. Thus, there is a continuing need to find alternative surfactants, particularly green chemistry surfactants that can still form a gel structure or a lamellar gel network matrix with $L_\beta$ phase in formulation and deliver the consumer-desired benefits. These alternative formulations that offer natural ingredients while still providing good consumer performance also require protection from microbial growth, and preferably while being free of preservatives. Thus, it is a continuing challenge to find natural materials or clean ingredients that are gentle, sustainably sourced, and environmental friendly that can provide an antimicrobial affect, while being compatible with the rest of the formulation and allowing the composition to deliver consumer benefits.

None of the existing art provides all of the advantages and benefits of the present invention, including performance, cost, safety, and being environmental-friendly.

SUMMARY OF THE INVENTION

The present invention is directed to a hair conditioning composition comprising a fatty acid, a fatty alcohol, and an antimicrobial system comprising glyceryl caprylate and one or more of 4-hydroxyacetophenone and pentylene glycol.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Q.S. herein means up to 100%.

Composition with Antimicrobial System

The hair conditioning composition of the present invention comprising:
- a) a fatty acid;
- b) a fatty alcohol; and
- c) an antimicrobial system comprising:
  - i) glyceryl caprylate; and
  - ii) one or more of 4-hydroxyacetophenone and pentylene glycol.

The objective of the invention is to provide stable conditioner compositions containing a gel structure or in some cases a lamellar gel network matrix with a $L_\beta$ phase. As consumers become more interested in products comprising only natural and gentle ingredients, the present inventors have devised formulations that rather than use a cationic surfactant molecule, comprise a fatty acid, a high melting point fatty alcohol, and a basic amino acid. This combination of a fatty alcohol, a fatty acid, and in some cases a basic amino acid with an aqueous carrier enables the preparation of lamellar sheet structures that allow a good rheology profile to provide good phase stability and conditioning benefits.

However, such a formulation may not itself be hostile to microbes. Use of known natural preservatives, such as sodium benzoate, may not be compatible with these formulations. Sodium benzoate, for example, can be incompatible in that it can result in a significant rheology reduction, even when used at a low level such as 0.8 wt %. As shown in Table 1, Comparative Example 1, which comprises a basic amino acid, a fatty acid, a fatty alcohol, and water, does not possess sufficient micro-hostility. Comparative Examples 2 and 3 further comprise a typical natural preservative, sodium benzoate, at 0.8 wt % and 3.5 wt %, respectively. While both Comparative Examples 2 and 3 showed sufficient micro-hostility, the sodium benzoate preservative was not ideally compatible with the formulation, as the compositions had a significant rheology drop of at least 50%.

TABLE 1

|  | Comparative Ex. 1 | Comparative Ex. 2 | Comparative Ex. 3 |
| --- | --- | --- | --- |
| Description | C18 Stearic Acid only; no preservative | C18 Stearic Acid only; 0.8% natural preservative S | C18 Stearic Acid only; 3.5% natural preservative S |
| L-Arginine | 0.22 | 0.22 | 0.22 |
| Stearic Acid* | 2.17 | 2.17 | 2.17 |
| Cetyl Alcohol | 1.75 | 1.75 | 1.75 |
| Stearyl Alcohol | 3.02 | 3.02 | 3.02 |
| Sodium Benzoate (S) | — | 0.80 | 3.50 |
| Water | Q.S, | Q.S, | Q.S. |
| MST Bacteria Day 2 | 0.8 | 1.5 | 5.2 |
| MST Bacteria Day 7 | 0.8 | 4.0 | 5.2 |
| MST Bacteria Day 28 | 0.8 | 5.2 | 5.2 |
| MST Yeast & Mold Day 14 | 1.3 | 4.8 | 5.7 |
| MST Yeast & Mold Day 28 | 1.3 | 5.7 | 5.7 |
| Overall MST Success Criteria Met | No | Yes | Yes |
| Rheology Shear Stress | 393 | 140 | 160 |
| Delta in Rheology % | NA | −64% | −59% |
| pH value | 6.2 | 5.4 | 5.5 |

*It has chain distribution of C16/C18 at around 50/50.

Therefore, there is a need to find natural materials that can provide the formulations of the present invention with an antimicrobial effect. The present invention involves hair care compositions that comprise ingredients that are compatible with a formulation comprising a fatty acid and a fatty alcohol, while providing a boost to microbial hostility and conditioning performance. In addition, these ingredients are clean ingredients, meaning that they are from sustainable sources and are environmentally friendly, while being completely safe to humans.

Glyceryl caprylate, 4-hydroxyacetophenone, and pentylene glycol each showed compatibility with formulations comprising a fatty alcohol and a fatty acid. That is, each indicated no significant rheology reduction and kept the creamy texture of the composition when made. Table 2 shows that hair conditioning formulations comprising a fatty acid and a fatty alcohol are compatible with these antimicrobial materials. Comparative Examples 4 and 5 show that formulations with glyceryl caprylate (Symlite G8) at 0.5 wt % and 0.8 wt % show no significant rheology reduction and keep the cream texture even after incorporation of the antimicrobial. Similarly, Comparative Examples 7 and 8, which comprise pentylene glycol (hydrolite green) at 3.0 wt % and 3.5 wt %, respectively, show compatibility by showing no significant reduction in rheology. Comparative Examples 9 and 10, comprising 4-hydroxyacetophenone (Symsave H), at 0.3 wt % and 0.8 wt % respectively, showed no significant rheology reduction and keep the cream texture even after incorporation of their ingredients. Only Comparative Example 5, which had a high level, 3.5 wt % of glyceryl caprylate, showed some incompatibility, as indicated by a low composition rheology.

TABLE 2

|  | Comp. Ex. 4 | Comp. Ex. 5 | Comp. Ex. 6 | Comp. Ex. 7 | Comp. Ex. 8 | Comp. Ex. 9 | Comp. Ex. 10 |
| --- | --- | --- | --- | --- | --- | --- | --- |
| Description | C18 Stearic Acid + 0.5 G ** only | C18 Stearic Acid + 0.8 G ** only | C18 Stearic Acid + 3.5 G ** only | C18 Stearic Acid + 3.0 P ** only | C18 Stearic Acid + 3.5 P ** only | C18 Stearic Acid + 0.3 H ** only | C18 Stearic Acid + 0.8 H ** only |
| L-Arginine | 0.22 | 0.22 | 0.22 | 0.22 | 0.22 | 0.22 | 0.22 |
| Stearic Acid* | 2.17 | 2.17 | 2.17 | 2.17 | 2.17 | 2.17 | 2.17 |
| Cetyl Alcohol | 1.75 | 1.75 | 1.75 | 1.75 | 1.75 | 1.75 | 1.75 |
| Stearyl Alcohol | 3.02 | 3.02 | 3.02 | 3.02 | 3.02 | 3.02 | 3.02 |
| 4-Hydroxyacetophenone (H) | — | — | — | — | — | 0.30 | 0.80 |
| Glyceryl caprylate (G) | 0.50 | 0.80 | 3.50 | — | — | — | — |
| Pentylene Glycol (P) | — | — | — | 3.00 | 3.50 | — | — |
| Water | Q.S, | Q.S, | Q.S, | Q.S, | Q.S, | Q.S, | Q.S, |
| Rheology Shear Stress | 435 | 376 | 181 | 307 | 323 | 405 | 407 |
| Delta in Rheology % | 10% | −4% | −54% | −21% | −18% | 3% | 4% |
| pH value | 6.0 | 6.0 | 5.9 | 6.1 | 6.2 | 6.0 | 5.9 |

*It has chain distribution of C16/C18 at around 50/50.
** Antimicrobial Key, Symsave H (H = 4-Hydroxyacetophenone), Symlite G8 (G = Glyceryl caprylate), Hydrolite Green (P = Pentylene Glycol).

Table 3 shows the potentiate antimicrobial effect of 0.5 wt % glyceryl caprylate (Symlite G8) when combined with 3.0 wt % pentylene glycol (hydrolite green) in Inventive Example 1, as compared to Comparative Examples 4, 6, 7, and 8. The MST data indicates superior antimicrobial effect while maintaining compatibility with a creamy texture as indicated by the rheology data. Furthermore, Inventive Example 1 and Comparative Examples 4 and 6 showed improved wet slip during application in comparison to Comparative Example 1, which is the composition without any preservative or antimicrobial material.

TABLE 3

|  | Comp. Ex. 4 | Comp. Ex 6 | Comp. Ex. 7 | Comp. Ex 8 | Ex. 1 |
| --- | --- | --- | --- | --- | --- |
| Description | Inventive example 1 C18 Stearic Acid + 0.5 G + 3.0 P ** | C18 Stearic Acid + 0.5 G ** only | C18 Stearic Acid + 3.5 G ** only | C18 Stearic Acid + 3.0 P ** only | C18 Stearic Acid + 3.5 P ** only | C18 Stearic Acid only; no preservative |
| L-Arginine | 0.22 | 0.22 | 0.22 | 0.22 | 0.22 | 0.22 |
| Stearic Acid* | 2.17 | 2.17 | 2.17 | 2.17 | 2.17 | 2.17 |
| Cetyl Alcohol | 1.75 | 1.75 | 1.75 | 1.75 | 1.75 | 1.75 |
| Stearyl Alcohol | 3.02 | 3.02 | 3.02 | 3.02 | 3.02 | 3.02 |
| Glyceryl caprylate (G) | 0.50 | 0.50 | 3.50 | — | — | — |

TABLE 3-continued

|  | Comp. Ex. 4 | Comp. Ex 6 | Comp. Ex. 7 | Comp. Ex 8 | Ex. 1 |
|---|---|---|---|---|---|
| Pentylene Glycol (P) | 3.00 | — | — | 3.00 | 3.50 | — |
| Water | Q.S, | Q.S, | Q.S, | Q.S, | Q.S, | Q.S, |
| MST Bacteria Day 2 | 5.2 | 3.5 | 5.2 | 1.0 | 1.4 | 0.8 |
| MST Bacteria Day 7 | 5.2 | 1.6 | 5.2 | 2.3 | 2.6 | 0.8 |
| MST Bacteria Day 28 | 5.2 | 1.4 | 1.7 | 5.2 | 5.2 | 0.8 |
| MST Yeast & Mold Day 14 | 4.4 | 2.1 | 2.1 | 1.3 | 1.3 | 1.3 |
| MST Yeast & Mold Day 28 | 4.9 | 2.5 | 2.5 | 1.4 | 2.6 | 1.3 |
| Overall Success Criteria Met | Yes | No | No | No | No | No |
| Rheology Shear Stress | 274 | 435 | 376 | 307 | 323 | 393 |
| Delta in Rheology % | −30% | 11% | −4% | −22% | −18% | NA |
| pH value | 6.0 | 6.0 | 5.9 | 6.1 | 6.2 | 6.2 |
| Wet Slip during application *** | D | D | D | C | C | C |

*It has chain distribution of C16/C18 at around 50/50.
** Antimicrobial Key, Symsave H (H = 4-Hydroxyacetophenone), Symlite G8 (G = Glyceryl caprylate), Hydrolite Green (P = Pentylene Glycol).
*** Control is the Ex. 1 C18 Stearic Acid Table 4 shows potentiate antimicrobial effect of 0.5 wt % glyceryl caprylate (Symlite G8) when combined with 0.3 wt % 4-hydroxyacetophenone (Symsave H) in Inventive Example 2, as compared to Comparative Examples 4, 5, and 9. The MST data indicates superior antimicrobial effect Example 9 just passes the success criteria, but it can be seen that when the antimicrobial system comprises not only 4-hydroxyacetophenone but 4-hydroxyacetophenon and glyceryl caprylate, such as Inventive Example 2, the antimicrobial effect is much stronger (5.2 vs. 2.9 on day 2).

TABLE 4

|  |  | Comp. Ex. 4 | Comp. Ex. 5 | Comp. Ex. 9 | Comp. Ex. 1 |
|---|---|---|---|---|---|
| Description | Inventive example 2 C18 Stearic Acid + 0.3 H + 0.5 G ** | C18 Stearic Acid + 0.5 G ** only | C18 Stearic Acid + 0.8 G ** only | C18 Stearic Acid + 0.3 H ** only | C18 Stearic Acid only; no preservative |
| L-Arginine | 0.22 | 0.22 | 0.22 | 0.22 | 0.22 |
| Stearic Acid* | 2.17 | 2.17 | 2.17 | 2.17 | 2.17 |
| Cetyl Alcohol | 1.75 | 1.75 | 1.75 | 1.75 | 1.75 |
| Stearyl Alcohol | 3.02 | 3.02 | 3.02 | 3.02 | 3.02 |
| 4-Hydroxyacetophenone (H) | 0.30 | — | — | 0.30 | — |
| Glyceryl caprylate (G) | 0.50 | 0.50 | 0.80 | — | — |
| Water | Q.S, | Q.S, | Q.S, | Q.S, | Q.S, |
| MST Bacteria Day 2 | 5.2 | 3.5 | 3.3 | 2.9 | 0.8 |
| MST Bacteria Day 7 | 5.2 | 1.6 | 3.2 | 4.9 | 0.8 |
| MST Bacteria Day 28 | 5.2 | 1.4 | 1.9 | 5.2 | 0.8 |
| MST Yeast & Mold Day 14 | 5.7 | 2.1 | 1.9 | 5.7 | 1.3 |
| MST Yeast & Mold Day 28 | 5.7 | 2.5 | 2.5 | 5.7 | 1.3 |
| Overall Success Criteria Met | Yes | No | No | Yes | No |
| Rheology Shear Stress | 318 | 435 | 376 | 405 | 393 |
| Delta in Rheology % | −19% | 11% | 4% | 3% | NA |
| pH value | 6.0 | 6.0 | 6.0 | 5.9 | 6.2 |
| Wet Slip during application *** | D | D | D | D | C |

*It has chain distribution of C16/C18 at around 50/50.
** Antimicrobial Key, Symsave H (H = 4-Hydroxyacetophenone), Symlite G8 (G = Glyceryl caprylate), Hydrolite Green (P = Pentylene Glycol).
*** Control is the Ex. 1 C18 Stearic Acid while maintaining compatibility with a creamy texture as indicated by the rheology data. Furthermore, Inventive Example 2 and Comparative Examples 4, 5, and 9 all showed improved wet slip during application in comparison to Comparative Example 1, which is the composition without any preservative or antimicrobial material. Comparative The inventive compositions herein may comprise from about 0.1 to about 3.5%, by weight of the composition, of glyceryl caprylate. The inventive compositions herein may comprise from about 0.1% to about 2% of 4-hydroxyacetophenone. The inventive compositions herein may comprise from about 2% to about 7% of pentylene glycol.

The ratio of glyceryl caprylate to 4-hydroxyacetophenone and/or pentylene glycol may be from about 1:1 or 1:10.

The inventive compositions herein may be free of any preservative. A preservative may be any material included in the EU Cosmetic Product Regulation, Annex V.

In some embodiments, other materials may be used in the antimicrobial system, additionally or as a substitute, that are chemically similar to glyceryl caprylate, 4-hydroxyacetophenone, and pentylene glycol, respectively. For example, glyceryl esters with C3-C14 carbon atom with an average molecular weight from 130 to about 310 daltons and having AlogP value from about −1.1 to about 4.7 may be used instead of, and at the same levels as, glyceryl caprylate. One or more of phenolic derivatives with an average molecular weight in acid form of from about 122 to about 180 daltons and AlogP value from about 0.33 to about 2.7 may be used instead of, and at the same levels as, 4-hydroxyacetophenone. And alkyl diol or triols with C3-C12 carbon chain with an average molecular weight from about 76 to about 210 daltons and AlogP value from about −1.4 to about 3.7 may be used instead of, and at the same levels as, pentylene glycol.

The possible glyceryl esters for use in the compositions herein may be included at a level of from about 0.1% to about 3.5%, preferably from about 0.5% to about 3.5%, by weight of the composition. The glyceryl esters are those having an average molecular weight of from about 130 to about 310 daltons, preferably from about 145 to 220 daltons, and having AlogP value from about −1.1 to about 4.7, from about −0.3 to about 2.0. Such glyceryl esters include, for example, those in the below table.

TABLE 5

| Glyceryl ester derivatives | Molecular Weight | ALogP |
|---|---|---|
| Glyceryl caprylate | 218.29 | 1.92 |
| Glyceryl Heptanoate | 204.26 | 1.46 |
| 2,3-Dihydroxypropyl decanoate | 246.34 | 2.83 |
| GLYCERYL 5-HYDROXYDECANOATE | 262.34 | 1.59 |
| 2,3-Dihydroxypropyl hexanoate | 190.24 | 1.01 |
| 2,3-Dihydroxypropyl 2-ethylhexanoate | 218.29 | 1.93 |
| Glyceryl 5-hydroxydodecanoate | 290.40 | 2.51 |
| 2,3-Dihydroxypropyl dodecanoate | 274.40 | 3.74 |
| 2,3-dihydroxypropyl nonanoate | 232.32 | 2.38 |
| Glyceryl 2-laurate | 274.40 | 3.74 |
| Glyceryl 2-caprate | 246.34 | 2.83 |
| 2,3-Dihydroxypropyl tetradecanoate | 302.45 | 4.66 |
| 1-Butyrylglycerol | 162.18 | 0.09 |
| Glycerol monoacetate | 134.13 | −1.03 |
| Glycerol propionate | 148.16 | −0.36 |
| glycerol benzoate | 196.20 | 0.64 |

Among them, preferred are those in the below table.

TABLE 6

| Preferred Glyceryl ester derivatives | Molecular Weight | ALogP |
|---|---|---|
| Glyceryl caprylate | 218.29 | 1.918 |
| Glyceryl Heptanoate | 204.2634 | 1.462 |
| 2,3-Dihydroxypropyl decanoate | 246.3431 | 2.831 |
| 2,3-Dihydroxypropyl hexanoate | 190.2368 | 1.006 |
| 2,3-Dihydroxypropyl dodecanoate | 274.3963 | 3.743 |
| 2,3-dihydroxypropyl nonanoate | 232.3166 | 2.375 |
| Glycerol monoacetate | 134.1305 | −1.03 |

TABLE 6-continued

| Preferred Glyceryl ester derivatives | Molecular Weight | ALogP |
|---|---|---|
| Glycerol propionate | 148.1571 | −0.363 |
| glycerol benzoate | 196.1999 | 0.635 |
| 2,3-Dihydroxypropyl 2-ethylhexanoate | 218.29 | 1.925 |

Among them, more preferred is that in the below table.

TABLE 7

| More Preferred Glyceryl ester derivatives | Molecular Weight | ALogP |
|---|---|---|
| Glyceryl caprylate | 218.29 | 1.918 |
| Glyceryl Heptanoate | 204.2634 | 1.462 |
| 2,3-Dihydroxypropyl hexanoate | 190.2368 | 1.006 |
| Glycerol propionate | 148.1571 | −0.363 |
| glycerol benzoate | 196.1999 | 0.635 |
| 2,3-Dihydroxypropyl 2-ethylhexanoate | 218.29 | 1.925 |

Among them, most preferred is that in the below table.

TABLE 8

| Most Preferred Glyceryl ester derivatives | Molecular Weight | ALogP |
|---|---|---|
| Glyceryl caprylate | 218.29 | 1.918 |
| Glyceryl Heptanoate | 204.2634 | 1.462 |

The possible phenolic derivatives for use in the compositions herein may be included at a level of from about 0.1% to about 2%, preferably from about 0.3% to about 0.8%, by weight of the composition. The phenolic derivatives are those having an average molecular weight of from about 122 to about 180 daltons, preferably from about 122 to 170 daltons, and having AlogP value from about 0.33 to about 2.7, from about 0.8 to about 2.0. Such phenolic derivatives include, for example, those in the below table.

TABLE 9

| Phenolic derivatives | Molecular Weight | ALogP |
|---|---|---|
| 4-Hydroxyacetophenone | 136.15 | 1.327 |
| 3-Hydroxyacetophenone | 136.15 | 1.327 |
| 4'-HYDROXYPROPIOPHENONE | 150.17 | 1.994 |
| 4-Hydroxybenzaldehyde | 122.12 | 1.347 |
| 4-Aminoacetophenone | 135.16 | 0.823 |
| Acetophenone, 4'-hydroxy-2-(methylamino)- | 165.19 | 0.798 |
| 2',4'-Dihydroxyacetophenone | 152.15 | 1.085 |
| 2'-Hydroxyacetophenone | 136.15 | 1.327 |
| Methyl 4-methylbenzoate | 150.17 | 2.7 |
| Ethanone, 2-amino-1-(3-hydroxyphenyl)- | 151.16 | 0.366 |
| Acetophenone, 2',5'-dihydroxy- | 152.15 | 1.085 |
| Ethanone, 1-(3,4-dihydroxyphenyl)- | 152.15 | 1.085 |
| 2'-HYDROXY-5'-METHYLACETOPHENONE | 150.17 | 1.814 |
| 2'-Amino-3'-hydroxyacetophenone | 151.16 | 0.581 |
| Acetophenone, 4'-hydroxy-3'-methoxy- | 166.1739 | 1.311 |
| 5-ACETYLSALICYLAMIDE | 179.1727 | 0.33 |
| 2'-HYDROXYPROPIOPHENONE | 150.1745 | 1.994 |

Among them, preferred are those in the below table.

TABLE 10

| Preferred Phenolic derivatives | Molecular Weight | ALogP |
|---|---|---|
| 4-Hydroxyacetophenone | 136.15 | 1.327 |
| 3-Hydroxyacetophenone | 136.15 | 1.327 |
| 4'-HYDROXYPROPIOPHENONE | 150.17 | 1.994 |
| 4-Hydroxybenzaldehyde | 122.12 | 1.347 |
| 4-Aminoacetophenone | 135.16 | 0.823 |
| Acetophenone, 4'-hydroxy-2-(methylamino)- | 165.19 | 0.798 |
| 2',4'-Dihydroxyacetophenone | 152.15 | 1.085 |
| 2'-Hydroxyacetophenone | 136.15 | 1.327 |
| Methyl 4-methylbenzoate | 150.17 | 2.7 |
| Ethanone, 2-amino-1-(3-hydroxyphenyl)- | 151.16 | 0.366 |
| Acetophenone, 2',5'-dihydroxy- | 152.15 | 1.085 |

Among them, more preferred is that in the below tables.

TABLE 11

| More Preferred Phenolic derivatives | Molecular Weight | ALogP |
|---|---|---|
| 4-Hydroxyacetophenone | 136.15 | 1.327 |
| 3-Hydroxyacetophenone | 136.15 | 1.327 |
| 4'-HYDROXYPROPIOPHENONE | 150.17 | 1.994 |
| 4-Hydroxybenzaldehyde | 122.12 | 1.347 |
| 4-Aminoacetophenone | 135.16 | 0.823 |
| Acetophenone, 4'-hydroxy-2-(methylamino)- | 165.19 | 0.798 |

Among them, most preferred is that in the below tables.

TABLE 12

| Most Preferred Phenolic derivatives | Molecular Weight | ALogP |
|---|---|---|
| 4-Hydroxyacetophenone | 136.15 | 1.327 |

The possible alkyl diol or triols for use in the compositions herein may be included at a level of from about 1% to about 7%, preferably from about 3% to about 3.5%, by weight of the composition. The alkyl diol or triols are those having an average molecular weight of from about 76 to about 210 daltons, preferably from about 76 to 150 daltons, and having AlogP value from about 1.5 to about 3.7, from about −0.9 to about 2.0. Such alkyl diol or triols include, for example, those in the below table.

TABLE 13

| Alkyl diol or triols derivatives | Molecular Weight | ALogP |
|---|---|---|
| Pentylene Glycol | 104.148 | 0.459 |
| 1,2-Hexanediol | 118.174 | 0.916 |
| 1,3-Hexanediol | 118.174 | 0.522 |
| 1,2,3-Hexanetriol | 134.174 | −0.051 |
| 1,2-Butanediol | 90.121 | 0.003 |
| 1,2,5-Pentanetriol | 120.147 | −0.766 |
| 1,2,6-Hexanetriol | 134.174 | −0.310 |
| 1,5-HEXANEDIOL | 118.174 | 0.578 |
| 1,3-Heptanediol | 132.201 | 0.978 |
| 1,2,4-Butanetriol | 106.120 | −1.346 |
| 1,3 BUTANEDIOL | 90.121 | −0.458 |
| 1,3-Butanediol, 2-ethyl- | 118.174 | 0.447 |
| 1,3-Pentanediol, 2-ethyl- | 132.201 | 0.971 |
| 2-Ethyl-1,3-hexanediol | 146.227 | 1.427 |
| 1,2-Heptanediol | 132.201 | 1.372 |
| 1,2-OCTANEDIOL | 146.227 | 1.828 |
| Decylene Glycol | 174.280 | 2.741 |

TABLE 13-continued

| Alkyl diol or triols derivatives | Molecular Weight | ALogP |
|---|---|---|
| Lauryl Glycol | 202.334 | 3.653 |
| 2,5-Hexanediol | 118.174 | 0.499 |
| 3-Methyl-1,3-butanediol | 104.148 | −0.253 |
| 1,4-Butanediol, 2-methyl- | 104.148 | 0.064 |
| 1,2-Ethanediol, 1-(2-piperidyl)- | 145.200 | −0.321 |
| Hexylene glycol | 118.174 | 0.124 |
| 1,2-propanediol | 76.09 | −0.9000 |

Among them, preferred are those in the below table.

TABLE 14

| Preferred Alkyl diol or triols derivatives | Molecular Weight | ALogP |
|---|---|---|
| Pentylene Glycol | 104.1476 | 0.459 |
| 1,2-Hexanediol | 118.1742 | 0.916 |
| 1,2,3-Hexanetriol | 134.1736 | −0.051 |
| 1,2-Butanediol | 90.121 | 0.003 |
| 1,2,5-Pentanetriol | 120.147 | −0.766 |
| 1,2,6-Hexanetriol | 134.1736 | −0.31 |
| 1,2,4-Butanetriol | 106.1204 | −1.346 |
| 1,2-Heptanediol | 132.2007 | 1.372 |
| 1,2-OCTANEDIOL | 146.2273 | 1.828 |
| Decylene Glycol | 174.2805 | 2.741 |
| Lauryl Glycol | 202.3336 | 3.653 |
| 1,2-Ethanediol, 1-(2-piperidyl)- | 145.1995 | −0.321 |
| 1,2-propanediol | 76.09 | −0.9 |

Among them, more preferred is that in the below tables.

TABLE 15

| More Preferred Alkyl diol or triols derivatives | Molecular Weight | ALogP |
|---|---|---|
| Pentylene Glycol | 104.1476 | 0.459 |
| 1,2-Hexanediol | 118.1742 | 0.916 |
| 1,2-Butanediol | 90.121 | 0.003 |
| 1,2-Heptanediol | 132.2007 | 1.372 |
| 1,2-OCTANEDIOL | 146.2273 | 1.828 |
| 1,2-propanediol | 76.09 | −0.9 |

Among them, most preferred is that in the below tables.

TABLE 16

| Most Preferred Alkyl diol or triols derivatives | Molecular Weight | ALogP |
|---|---|---|
| Pentylene Glycol | 104.1476 | 0.459 |

LAMELLAR GEL NETWORK MATRIX WITH a $L_\beta$ PHASE or Gel Structure

The compositions of the present invention comprise a gel structure or in some cases a lamellar gel network matrix with a $L_\beta$ phase. The lamellar gel network matrix with a $L_\beta$ phase, sometimes referred to as a gel network or gel matrix, may comprise the fatty acid, fatty alcohol, basic amino acid, and an aqueous carrier. The gel structure or lamellar gel network matrix with a $L_\beta$ phase is suitable for providing various conditioning benefits, such as slippery feel during the application to wet hair and softness and moisturized feel on dry hair.

The antimicrobial systems of the present invention work in hair conditioner compositions comprising a fatty acid and a fatty alcohol, meaning there is sufficient antimicrobial effect. To achieve a gel structure or lamellar gel network, the composition may further comprise a base, in some cases a basic amino acid. In other embodiments, the base may be, but is not limited to, hydroxyethyl urea, or di-amines that are not basic amino acids, or in some cases sodium hydroxide. In other cases, a gel network may be formed with the fatty acid, fatty alcohol, aqueous carrier, and a cationic surfactant such as BTMAC/SAPMDA, plus the antimicrobial system described herein.

The gel structure or lamellar gel network matrix with a $L_\beta$ phase of the inventive hair conditioner compositions may comprise a surfactant that comprises a basic amino acid and longer alkyl chain of a fatty acid that contain C10-C22 as major chain length.

The composition may comprise from about 0.01% to about 15% of the basic amino-acid, by weight of the hair conditioner composition. In some embodiments, the amount of the basic amino acid may be from about 0.01% to about 15%, preferably from about 0.03% to about 10%, more preferably from about 0.1% to about 6%, by weight of the hair conditioner composition. In some embodiments, the basic amino acid comprises more than two amine groups. Suitable basic amino acids may include, but are not limited to, arginine, lysine, histidine, poly-amino acids, and combinations thereof. In some embodiments, additional amino acids may be added, including poly-amino acids. Poly-amino acids may be added up to a 1:1 ratio with other amino acids. The iso-electrostatic point for each amino acid, and for all amino acids when combined may be at least about 7. In some embodiments, the composition may further comprise di-amines that are not basic amino acids, such as hydroxyethyl urea. The basic amino acids of the present invention may be combined with a fatty acid at certain pH and processing conditions to form a lamellar gel network matrix with a $L_\beta$ phase. The composition may comprise from about 0.01% to about 15% of the fatty acid, by weight of the hair conditioner composition. In some embodiments, the amount of the fatty acid may be from about 0.01% to about 15%, preferably from about 0.05% to about 10%, more preferably from about 0.1% to about 5%, by weight of the hair conditioner composition. The fatty acid may comprise saturated and/or unsaturated fatty acids. The ratio of saturated fatty acids to unsaturated fatty acids may be from about 8:1 to about 1:4, or from about 4:1 to about 1:2. In some embodiments, the fatty acid may comprise from about 0.3% to about 5% of unsaturated fatty acid, by weight of the hair conditioner composition. The fatty acid may have C10-C22 alkyl chains, in some cases C16-C22 alkyl chains, and in still other cases C18-C22 alkyl chains as the main components. The saturated fatty acid may include, but is not limited to, stearic acid (with C16/18 chain distribution), palmitic acid, behenic acid, and combinations thereof. The unsaturated fatty acid may include, but is not limited to, rapeseed acid, oleic acid, linoleic acid, and combinations thereof.

In some embodiments, use of fatty acids having C12-C14 alkyl chains may improve the wet detangling of the hair conditioning composition, while maintaining a clean feel.

In some embodiments, compositions comprising C12-C14 shorter fatty acid alkyl chains can provide improved wet and dry conditioning, in combination with high levels of arginine.

However, in some embodiments, compositions comprising longer fatty acid chains, such as C22, may provide a coated dry conditioning feel without a greasy residue feel, especially for highly damaged hair.

In some embodiments, the surfactant may further comprise cationic surfactants in addition to a basic amino acid. Suitable cationic surfactants may include, for example, behentrimonium methosulfate (BTMS), behentrimonium chloride (BTMAC), stearamidopropyldimethylamine (SAPDMA), behenamidopropyldimethylamine (BAPDMA), brassicyl valinate esylate, and combinations thereof.

The hair conditioner compositions may comprise at least about 60% of an aqueous carrier, by weight of said hair conditioner composition, and in some embodiments at least about 80%.

The gel structure or lamellar gel network matrix with a $L_\beta$ phase may comprise a fatty acid, high melting point fatty alcohol, basic amino acid, and an aqueous carrier. In general, the mixture of the basic amino acid and the fatty acid, along with the aqueous carrier, may have a pH of at least about 4.5. The ratio of basic amino acid to the fatty acid may be from about 1:40 to about 40:1, preferably from about 1:15 to about 30:1, or more preferably from about 1:10 to about 20:1.

In some embodiments, the ratio of the sum of the basic amino acid (a) plus fatty acid (b) to the sum of the basic amino acid (a), fatty acid (b), and fatty alcohol (c), by weight ((a+b)/(a+b+c)), may be from about 0.1 to about 0.9, preferably from about 0.20 to about 0.5. In some embodiments, the conditioner composition may comprise from about 6% to about 20%, by weight of the composition, of the basic amino acid plus fatty acid plus fatty alcohol. These ratios and weight percents may provide better detangling and also a more robust lamellar gel network matrix with a $L_\beta$ phase structure.

The compositions of the present invention may be substantively free of ceramide. The compositions of the present invention may be substantively free of cholesterol. And the compositions of the present invention may be substantively free of a gel network made of only non-ionic surfactant.

High Melting Fatty Alcohol

The high melting point fatty alcohol can be included in the composition at a level of from about 2%, preferably from about 4%, more preferably from about 5%, still more preferably from about 5.5%, and to about 15%, preferably to about 10% by weight of the composition, in view of providing the benefits of the present invention.

The high melting point fatty alcohol useful herein have a melting point of 25° C. or higher, preferably 40° C. or higher, more preferably 45° C. or higher, still more preferably 50° C. or higher, in view of stability of the lamellar gel network matrix with LP. Preferably, such melting point is up to about 90° C., more preferably up to about 80° C., still more preferably up to about 70° C., even more preferably up to about 65° C., in view of easier manufacturing and easier emulsification. In the present invention, the high melting point fatty alcohol can be used as a single alcohol or as a blend or mixture of at least two high melting point fatty alcohols. When used as such blend or mixture, the above melting point means the melting point of the blend or mixture.

The high melting point fatty alcohol useful herein is selected from the group consisting of fatty alcohols, fatty alcohol derivatives, fatty acid derivatives, and mixtures thereof. It is understood by the artisan that the alcohols disclosed in this section of the specification can in some instances fall into more than one classification, e.g., some fatty alcohol derivatives can also be classified as fatty acid derivatives. However, a given classification is not intended to be a limitation on that particular alcohol but is done so for convenience of classification and nomenclature. Further, it is understood by the artisan that, depending on the number and position of double bonds, and length and position of the branches, certain alcohols having certain required carbon atoms may have a melting point of less than the above preferred in the present invention. Such alcohols of low melting point are not intended to be included in this section. Nonlimiting examples of the high melting point alcohols are found in International Cosmetic Ingredient Dictionary, Fifth Edition, 1993, and CTFA Cosmetic Ingredient Handbook, Second Edition, 1992.

The high melting point fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These alcohols are known to have the above melting point. However, they often have lower melting points when supplied, since such supplied products are often mixtures of fatty alcohols having alkyl chain length distribution in which the main alkyl chain is a cetyl, stearyl or behenyl group. In the present invention, more preferred fatty alcohols are cetyl alcohol, stearyl alcohol and mixtures thereof.

Commercially available high melting point fatty alcohols useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan).

Together with a high melting point fatty alcohol, the compositions can further comprise a low melting fatty alcohol, for example, oleyl alcohol.

Aqueous Carrier

The conditioning composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 70% to about 90% water.

Silicone Compound

The compositions of the present invention may, or may not, contain a silicone compound. It is believed that the silicone compound can provide smoothness and softness on dry hair. The silicone compounds herein can be used at levels by weight of the composition of preferably from about 0.1% to about 20%, more preferably from about 0.5% to about 10%, still more preferably from about 1% to about 8%.

Preferably, the silicone compounds have an average particle size of from about 1 micron to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):

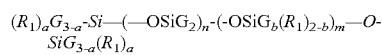

$(R_1)_a G_{3-a}\text{-Si}\text{---}(\text{---OSiG}_2)_n\text{-}(\text{-OSiG}_b(R_1)_{2-b})_m\text{---}O\text{-}SiG_{3-a}(R_1)_a$ wherein G is hydrogen, phenyl, hydroxy, or C1-C$_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; R$_1$ is a monovalent radical conforming to the general formula CqH$_{2q}$L, wherein q is an integer having a value from 2 to 8 and L is selected from the following groups: —N(R$_2$)CH$_2$—CH$_2$—N(R$_2$)$_2$; —N(R$_2$)$_2$; —N(R$_2$)$_3$A$^-$; —N(R$_2$)CH$_2$—CH$_2$—NR$_2$H$_2$A$^-$; wherein R$_2$ is hydrogen, phenyl, benzyl, or a saturated hydrocarbon radical, preferably an alkyl radical from about C$_1$ to about C20; A$^-$ is a halide ion.

Highly preferred amino silicones are those corresponding to formula (I) wherein m=0, a=1, q=3, G=methyl, n is preferably from about 1500 to about 1700, more preferably about 1600; and L is —N(CH3)2 or —NH2, more preferably —NH2. Another highly preferred amino silicones are those corresponding to formula (I) wherein m=0, a=1, q=3, G=methyl, n is preferably from about 400 to about 600, more preferably about 500; and L is —N(CH3)2 or —NH2, more preferably —NH2. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning. Some embodiments may include Silicone Quaternium-26.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; pH adjusting agents, such as citric acid, sodium citrate, succinic acid, phosphoric acid, sodium hydroxide, sodium carbonate; coloring agents, such as any of the FD&C or D&C dyes; perfumes; and sequestering agents, such as disodium ethylenediamine tetra-acetate; ultraviolet and infrared screening and absorbing agents such as benzophenones; and antidandruff agents such as zinc pyrithione.

Low Melting Point Oil

The compositions may comprise one or more conditioning oils. Low melting point oils useful herein are those having a melting point of less than 25° C. The low melting point oil useful herein is selected from the group consisting of: hydrocarbon having from 10 to about 40 carbon atoms; unsaturated fatty alcohols having from about 10 to about 30 carbon atoms such as oleyl alcohol; unsaturated fatty acids having from about 10 to about 30 carbon atoms; fatty acid derivatives; fatty alcohol derivatives; ester oils such as pentaerythritol ester oils including pentaerythritol tetraisostearate, trimethylol ester oils, citrate ester oils, and glyceryl ester oils; poly α-olefin oils such as polydecenes; and mixtures thereof. Additional oils may include triglycerides, such as caprylic capric triglyceride or vegetable oils such as coconut oil, soybean oil, rapeseed oil, cocoa butter, olive oil, palm oil, rice bran oil, and mixtures thereof.

In some embodiments, a conditioning oil may have a hydrophilic-lipophilic balance (HLB) of less than about 10. In some embodiments, the oil may be a mono, di, or tri ester or ether where the monomer units have a carbon chain of C2 to C16, preferably C4 to C10, or more preferably C6 to C8. In some embodiments, the oil may be a polyester with the hydrophobic monomer units (linear or branched) having carbon chains shorter than C16, preferably shorter than C12. Commercially available oil examples include, but are not limited to, Myritol 318 from BASF (caprylic/capric triglyceride), Plantasil Micro from BASF (dicaprylyl ether in emulsion form (Dicaprylyl Ether (and) Decyl Glucoside (and) Glyceryl Oleate)); or Citropol 1A from P2 science (Polycitronellol Acetate).

Product Forms

The conditioning compositions of the present invention can be in the form of rinse-off products or leave-on products and can be formulated in a wide variety of product forms, including but not limited to pastes, creams, gels, emulsions, mousses, and sprays. The conditioning composition of the present invention is especially suitable for a rinse-off hair conditioner or for a no-rinse hair conditioner.

Method of Use

The conditioning composition of the present invention is preferably used for a method of conditioning hair, the method comprising following steps:

(i) after shampooing hair, applying to the hair an effective amount of the conditioning composition for conditioning the hair; and (ii) optionally, then rinsing the hair.

Effective amount herein is, for example, from about 0.1 ml to about 2 ml per 10 g of hair, preferably from about 0.2 ml to about 1.5 ml per 10 g of hair.

The conditioning composition of the present invention provides improved conditioning benefits, especially improved wet conditioning benefits after rinsing and improved dry conditioning, while maintaining wet conditioning benefit before rinsing. The conditioning composition of the present invention may also provide improved product appearance to consumer. Thus, a reduced dosage of the conditioning composition of the present invention may provide the same level of conditioning benefits as those of a full dosage of conventional conditioner compositions. Such reduced dosage herein is, for example, from about 0.3 ml to about 0.7 ml per 10 g of hair.

Method of Manufacturing

The present invention is also directed to a method of manufacturing a hair conditioning composition as follows:
a) Add water that is at a temperature higher than the temperature of the melting point of the fatty acid and the fatty alcohol, and mixture of them (about 80° C.-90° C.);
b) Add base or basic amino acid in hot water (about 80° C.-90° C.);
c) Prepare a homogeneous premix of the fatty acid and a fatty alcohol at a temperature that is higher than either of their individual melting points and add it into the hot water (about 80° C.-90° C.);
d) Cool the mixture below the phase transition temperature to form a gel structure or a gel network matrix; and
e) add antimicrobials.

Alternatively, the antimicrobials may be added before the cooling, after step a) or after step d), for example, or one or more antimicrobial may be added before the cooling and one or more antimicrobial added after the cooling. Or, the antimicrobials may all be added after the cooling and gel formation, as was done in the Inventive Examples. The method may further comprise the steps of adding additional ingredients such as silicone or oil compounds, perfumes, esthetics if included. The inventive conditioning compositions of the present invention can also be prepared by any conventional method well known in the art.

The pH of the finished product and of the composition during the making process after the cooling down step may be at least 4.5.

Test Methods

1. Wet Expert Sensory Method

This is expert sensory panel test method uses three highly expert sensory panel to evaluate specific attribute during wet stage hair treatment. The treatment protocol for the hair treatment is stated as follow:
a. Rinse 20 g of hair switches with water and squeeze water out from top to bottom once.
b. 1 ml conditioner was applied front and 1 ml conditioner was applied back.
c. Lather the product 30 strokes for 30 seconds on hair switch.
d. The hair was then rinse for 15 seconds front and 15 seconds back, and squeeze water out from top to bottom once.

The sensory attribute evaluated during wet stage is mentioned below:

Wet Slip during application: Panellist will evaluate the finger speed from top to bottom of wet hair during application of 30 strokes on hair switch.

The score rating for the attribute is compared to the Control mentioned in each table. Each category score is considered a meaningful difference from the other and shows that the attribute evaluated by all three highly sensitive panellist is consistent. A mix score data between the panellist, the score placed will be at lower score.
A=Significant lower intensity to attribute
B=Significant lower intensity to attribute
C=Equal intensity to attribute
D=Significant higher intensity to attribute
E=Obvious Significant higher intensity to attribute 2. Rheology Test Method Rheology is used to evaluate and characterise product samples. The two key rheology methods identified are mentioned below:

Shear Stress at 950 s$^{-1}$ via flow curve: This is the method to ramp up shear rate logarithmically from 0.1 to 1000 s$^{-1}$ in 1 min using a cone & plate geometry, and to read the shear stress value 6 (Pa) at shear rate 950 s$^{-1}$.

Delta in Rheology %: This is the percentage difference in rheology measurement following the formula below:

Delta in Rheology %=$((a-b)/b) \times 100\%$ where a is the post added product and b is the no post added product. If rheology reduction is more than 50%, it would indicate significant interaction with chassis and incompatible.

3. pH Value Test Method

A pH test method measures the hydrogen-ion activity in water-based solutions, indicating its acidity or alkalinity expressed as pH value. The product is kept at room temperature which will then be measured pH. The acceptable range for pH value is from 3 until 9.

4. Micro Susceptibility Test (MST) Harmonized Method

During development, P&G Microbial Susceptibility Test (MST, GCAS 96366921) is the main method used. Briefly, 2 separate pools of challenge organisms, Bacterial pool: *Staphylococcus aureus, Pseudomonas aeruginosa, Escherichia coli, Burkholderia capacia, Klebsiella pneumoniae, Enterobacter gergoviae* and *Serratia marcescens*; Yeast and Mold pool: *Candida albicans* and *Aspergillus brasiliensis* were added to the test product to simulate potential consumer contaminations. The microbial challenge level in test product for each pool is 105-107 CFU/g. The microbial content of the inoculated test product was subsequently evaluated over the next four weeks at multiple time points using microbiological plate count. Serial dilution and preservative neutralization were accomplished with nutritive bases before plating. Product is deemed to have passed MST if the success criteria below are met:

|  | Day 2 | Day 7 | Day 14 | Day 28 |
| --- | --- | --- | --- | --- |
| Bacteria | ≥2 log reduction | ≥3 log reduction | None | No decrease from Day 7 |
| Yeast/Mold |  | None | ≥2 log reduction | No decrease from Day 14 |

MST Bacteria Day 2: The log reduction should be equal or more than 2 at Day 2 of sampling to meet the success criteria.

MST Bacteria Day 7: The log reduction should be equal or more than 3 at Day 7 of sampling MST Bacteria Day 28: The log reduction at day 28 should show no decrease from Day 7 to meet the success criteria.

MST Yeast & Mold Day 14: The log reduction at should be equal or more than 2 at Day14 of sampling to meet the success criteria.

MST Yeast & Mold Day 28: The log reduction at day 28 should show no decrease from Day 14 to meet the success criteria.

Description Overall Success Criteria Met: When all four weeks for each or combined preservative system meets the success criteria, it will be stated as Yes. If at any weekly time-point the preservative system does not meet the success criteria, it will be stated as No.

Examples/Combinations
A. A hair conditioner composition comprising:
   a) a fatty acid;
   b) a fatty alcohol; and
   c) an antimicrobial system comprising:
      i) glyceryl caprylate; and
      ii) one or more of 4-hydroxyacetophenone and pentylene glycol.
B. The composition of paragraph A, further comprising a basic amino acid.
C. The composition of paragraph B, further comprising an aqueous carrier.
D. The composition of any one of paragraphs A to C, wherein the composition comprises from about 0.1 to about 3.5%, by weight of the composition, of glyceryl caprylate.
E. The composition of any one of paragraphs A to D, wherein the composition comprises from about 0.1% to about 2% of 4-hydroxyacetophenone.
F. The composition of any one of paragraphs A to E, wherein the composition comprises from about 2% to about 7% of pentylene glycol.
G. The composition of any one of paragraphs A to F, wherein the composition comprises a gel structure or a lamellar gel network matrix with a $L_\beta$ phase.
H. The composition of any one of paragraphs C to G, wherein the basic amino acid, fatty acid, and aqueous carrier combined have a pH of at least about 4.5.
I. The composition of any one of paragraphs C to H, wherein the hair conditioner composition comprises from about 0.01% to about 15% of the basic amino acid, by weight of the hair conditioner composition.
J. The composition of any one of paragraphs C to I, wherein the hair conditioner composition comprises from about 0.01% to about 15% of fatty acids, by weight of the hair conditioner composition.
K. The composition of any one of paragraphs C to J, wherein the hair conditioner composition comprises at least about 60% of an aqueous carrier, by weight of said hair conditioner composition.
L. The composition of any one of paragraphs A to K, wherein the fatty acid comprises saturated and unsaturated fatty acids, wherein the ratio of saturated fatty acids to unsaturated fatty acids is from about 8:1 to about 1:4.
M. The composition of any one of paragraphs A to L, wherein the composition further comprises a conditioning oil.
N. The composition of paragraph M, wherein the conditioning oil is a non-silicone.
O. The composition of any one of paragraphs M and N, wherein the conditioning oil is in preformed emulsion form, with a particle size at most about 500 nm.
P. The composition of any one of paragraphs M to 0, wherein the conditioning oils have an HLB of less than about 10.
Q. The composition of any one of paragraphs C to P, wherein the basic amino acid is selected from the group consisting of arginine, lysine, histidine, and combinations thereof.
R. The composition of any one of paragraphs A to Q, wherein the fatty acid has C10-C22 alkyl chains.
S. The composition of any one of paragraphs A to R, wherein the composition is free of a preservative.
T. The composition of any one of paragraphs A to S, wherein the ratio of antimicrobial system c(i) to antimicrobial system c(ii) are 1:1 to 1:10.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioner composition comprising:
   a) a fatty acid;
   b) a fatty alcohol; and
   c) an antimicrobial system comprising:
      i) glyceryl caprylate; and
      ii) one or more of 4-hydroxyacetophenone and pentylene glycol; and
   d) about 0.22% arginine,
   wherein the hair conditioner composition comprises a gel structure or a lamellar gel network matrix with a $L_\beta$ phase; and
   wherein the hair conditioner composition is substantively free of cholesterol.

2. The hair conditioner composition of claim 1, further comprising an aqueous carrier.

3. The hair conditioner composition of claim 1, wherein the hair conditioner composition comprises from about 0.1 to about 3.5%, by weight of the hair conditioner composition, of glyceryl caprylate.

4. The hair conditioner composition of claim 1, wherein the hair conditioner composition comprises from about 0.1% to about 2% of 4-hydroxyacetophenone.

5. The hair conditioner composition of claim 1, wherein the hair conditioner composition comprises from about 2% to about 7% of pentylene glycol.

6. The hair conditioner composition of claim 2, wherein the arginine, fatty acid, and aqueous carrier combined have a pH of at least about 4.5.

7. The hair conditioner composition of claim 2, wherein the hair conditioner composition comprises from about 0.01% to about 15% of fatty acids, by weight of the hair conditioner composition.

8. The hair conditioner composition of claim 2, wherein the hair conditioner composition comprises at least about 60% of the aqueous carrier, by weight of said hair conditioner composition.

9. The hair conditioner composition of claim 1, wherein the fatty acid comprises saturated and unsaturated fatty acids, wherein weight ratio of the saturated fatty acids to the unsaturated fatty acids is from about 8:1 to about 1:4.

10. The hair conditioner composition of claim 2, wherein the hair conditioner composition further comprises a conditioning oil.

11. The hair conditioner composition of claim 10, wherein the conditioning oil is a non-silicone.

12. The hair conditioner composition of claim 10, wherein the conditioning oil is in preformed emulsion form, with a particle size at most about 500 nm.

13. The hair conditioner composition of claim 10, wherein the conditioning oil has an HLB of less than about 10.

14. The hair conditioner composition of claim 1, wherein the fatty acid has C10-C22 alkyl chains.

15. The hair conditioner composition of claim 1, wherein the hair conditioner composition is free of a preservative.

16. The hair conditioner composition of claim 1, wherein weight ratio of the antimicrobial system c)i) to the antimicrobial system c)ii) is 1:1 to 1:10.

\* \* \* \* \*